United States Patent [19]

Jensen

[11] Patent Number: 5,411,542
[45] Date of Patent: May 2, 1995

[54] POST-OPERATIVE THERMAL BLANKET FOR ANKLE AND FOOT

[75] Inventor: Marvin E. Jensen, Mundelein

[73] Assignee: Hollister Incorporated, Libertyville, Ill.

[21] Appl. No.: 139,287

[22] Filed: Oct. 20, 1993

[51] Int. Cl.⁶ .............................................. A61F 7/00
[52] U.S. Cl. ................................. 607/104; 607/111; 607/112; 126/204; 165/46
[58] Field of Search .................. 607/96, 108–112, 607/114, 104, 107; 62/259.3; 165/46; 126/204

[56] References Cited

U.S. PATENT DOCUMENTS

| | | | |
|---|---|---|---|
| 2,299,162 | 5/1941 | Marick | 607/108 |
| 3,178,559 | 4/1965 | Fogel et al. | 219/527 |
| 4,061,898 | 12/1977 | Murray et al. | 219/211 |
| 4,085,620 | 2/1989 | Meistrell | 128/402 |
| 4,114,620 | 9/1978 | Moore et al. | 128/254 |
| 4,118,946 | 10/1978 | Tubin | 62/514 R |
| 4,149,541 | 4/1979 | Gammons et al. | 128/400 |
| 4,172,495 | 10/1979 | Zebuhr et al. | 156/46 |
| 4,382,446 | 5/1983 | Truelock et al. | 607/110 |
| 4,765,338 | 8/1988 | Turner et al. | 607/110 |
| 4,951,665 | 8/1990 | Schneider | 128/400 |
| 4,982,736 | 1/1991 | Schneider | 128/400 |
| 5,133,348 | 7/1992 | Mayn | 607/108 |
| 5,190,032 | 3/1993 | Zacoi | 128/400 |
| 5,230,335 | 7/1993 | Johnson, Jr. et al. | 128/400 |
| 5,241,951 | 9/1993 | Mason et al. | 607/104 |

Primary Examiner—Lee S. Cohen
Assistant Examiner—Robert L. Nasser, Jr.
Attorney, Agent, or Firm—Tilton Fallon, Lungmus

[57] ABSTRACT

A thermal blanket particularly suitable for post-operative treatment of the ankle and foot. The blanket includes inner and outer panels of easily foldable material having an outline defining two foot sections, an ankle section, and a T-shaped leg encircling section. The outer panel has its entire outer surface formed of soft loop pile fabric and the inner panel is composed of double layers of thermoplastic sheet material heat-sealed together to define at least one and preferably two serpentine flow passages for the circulation of thermal fluid through the blanket. The foot sections have bottom edges joined by one or more elastic webs. Hook-providing attachment patches, releasably attachable to the loop pile fabric that forms the entire outer surface of all of the sections of the blanket, detachably secure the upper edges of the foot sections together, as well as the front edges of the ankle section and the ends of the band portion of the T-shaped section, when the blanket is worn.

13 Claims, 2 Drawing Sheets

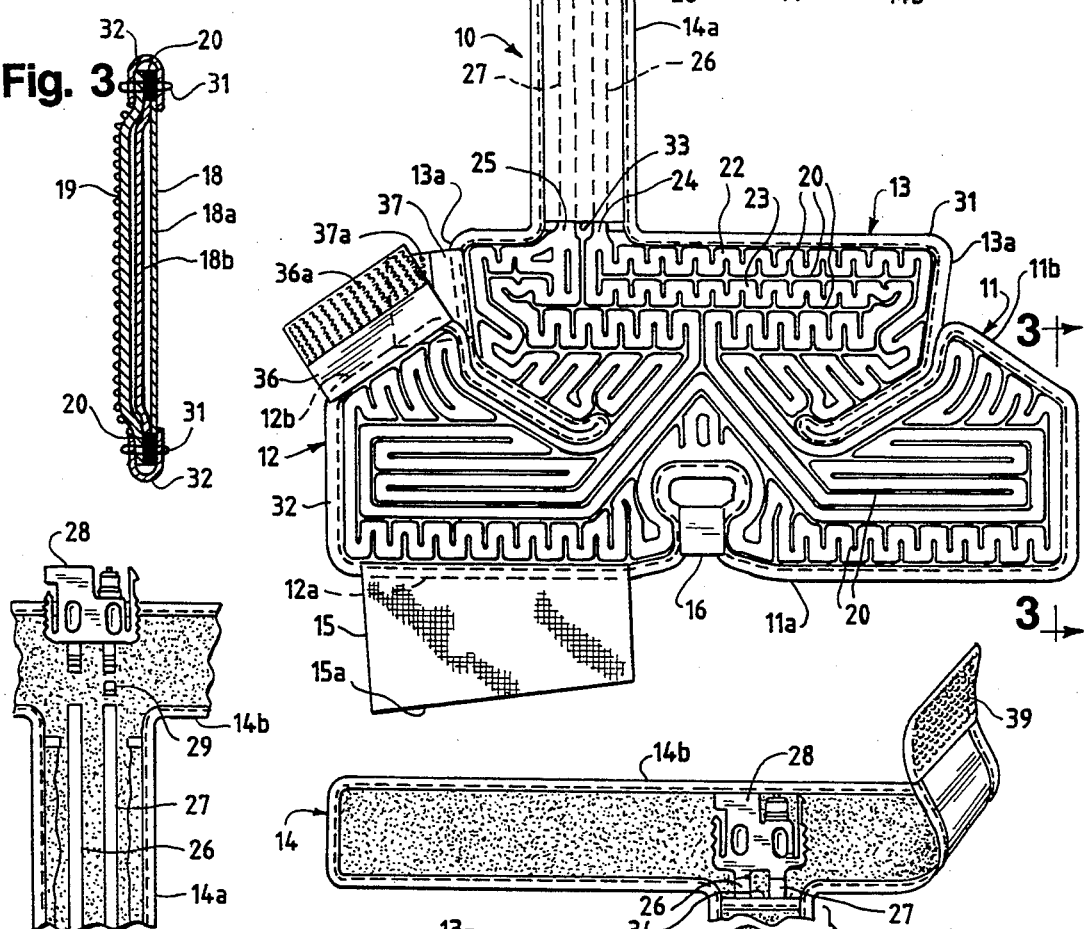

POST-OPERATIVE THERMAL BLANKET FOR ANKLE AND FOOT

BACKGROUND AND SUMMARY

The therapeutic use of thermal blankets having walls of flexible polymeric material that are sealed together to define a labyrinth of passages for the circulation of heating or cooling fluid is well known. While such therapy may involve either heating or cooling portions of the body, it is the cooling mode that in recent years has received particular attention because of its effectiveness in post-operative treatment and in connection with physical therapy. In particular, cryotherapy following soft tissue trauma has been shown to reduce pain, swelling blood loss, inflammation and hematoma formation. During the rehabilitative process, cryotherapy has been utilized effectively to diminish inflammation and patient discomfort.

For such therapy, the thermal blanket should fit snugly about and uniformly contact the area of the body requiring treatment. Where the treatment site is relatively flat, or is of regular contour, these objectives may be accomplished with a blanket that normally lies flat and can be placed against, or wrapped about, the body part. However, such objectives are far more difficult to achieve when a body portion to receive thermal treatment is a joint area of complex and variable curvatures such as the ankle and foot.

The problems of providing effective cryotherapy (or heat therapy) to such a joint area using a blanket having fluid circulation passages are further complicated by the difficulties of insuring proper flow throughout the blanket when it has been folded or wrapped about the treatment site. If, for example, the blanket is of a type that allows thermal fluid to flow at random because the thermoplastic layers are joined together at a multiplicity of points that do not provide clearly-defined flow routes, then, when such a blanket is wrapped or folded about the treatment site, the thermal fluid can be expected to take paths of least resistance and certain areas of the blanket may receive little or no fluid circulation. On the other hand, if the blanket is of a type that has clearly defined (i.e., tubular) flow passages, there is a risk that such passages may become kinked and obstruct fluid flow when the blanket is folded or wrapped about the treatment site.

All such blankets that provide for the circulation of thermal fluid have inlet and outlet tubes leading to and from the cooling/heating/pumping equipment that controls fluid temperature and directs flow circulation. Such tubes, and the inlet and outlet passages of the blanket with which they communicate, are vulnerable to kinking and twisting that might result in flow obstruction as the patient moves about or changes body position during waking hours and in particular, during sleep, when such obstruction of the passages may go unnoticed.

Accordingly, an important aspect of this invention lies in providing a blanket that is particularly suitable for thermal treatment of the ankle and foot and may be easily adjusted to fit patients of different size and physical characteristics notwithstanding the fact that the blanket is manufactured in substantially flat or planar condition. A zigzag arrangement of dual passages extends through the blanket in directions that eliminate or greatly reduce possibilities of partial or total flow obstruction since, by reason of such arrangement, forces imposed on the passages when the blanket is properly wrapped about the foot and ankle tend to be in the form of twisting rather than kinking forces. Kinking of inlet and outlet tubes and the inlet/outlet passages of the blanket with which they communicate is prevented by providing the blanket with an integral leg wrap that supports the tubes and the fluid coupling element(s) connected to them and immobilizes such tubes and element(s) in relation to the patient's leg. Close fitting of the blanket to the treatment site is assured by providing the blanket with an outline of distinctive and developed shape in which certain sections are connected by one or more elastic webs, by utilizing Velcro-type hook and loop attachment means, and by providing substantially the entire outer (exterior) panel of the blanket with a soft loop-providing pile fabric which constitutes the loop component of the hook-loop attachment system.

Briefly, the foot and ankle blanket is composed of inner and outer panels of easily foldable material having an outline defining two foot sections (lateral and medial) and an ankle section integral therewith. The outer panel has its entire outer surface formed of soft loop pile fabric and the inner panel is composed of double layers of thermoplastic sheet material heat-sealed together to define at least one (most advantageously two) serpentine flow passage(s) extending along a zigzag pathway from an inlet opening to an adjacent outlet opening. The foot sections have bottom edges joined by at least one (preferably two) two-way stretch elastic web(s) positioned to underlie a patient's foot and extend behind the heel when the blanket is worn. A T-shaped leg wrap is formed integrally with the ankle section and includes an upwardly-extending strap portion which contains the inlet and outlet tubes for the blanket. At its top, the T-shaped section includes a band portion that wraps about the lower portion of the wearer's leg and attaches to itself to maintain the inlet-outlet tubes in untwisted and unkinked condition. Velcro-type hook patches are provided by one of the foot sections, the ankle section, and the strap portion of the T-shaped section, for holding the blanket in snug, slightly tensioned, and elastically conformable condition about a wearer's foot and ankle, thereby insuring effective thermal treatment when the blanket is in use.

Other features, objects, and advantages will become apparent from the specification and drawings.

DRAWINGS

FIG. 1 is a plan view of the foot and ankle blanket showing the inner body-engaging surface thereof. The blanket is shown in planar condition just prior to a final manufacturing step in which a second edge of an elastic web is secured to a lower edge of one of the foot sections of the blanket.

FIG. 2 is a top plan view of the blanket depicted in FIG. 1.

FIG. 3 is an enlarged and somewhat schematic sectional view taken along line 3—3 of FIG. 1.

FIG. 4 is a fragmentary top plan view, partially cut away and exploded, to illustrate the relationship between the blanket, its inlet and outlet tubes, and a fluid coupling element equipped with a flow restrictor.

DETAILED DESCRIPTION OF PREFERRED EMBODIMENT

Figure 6:
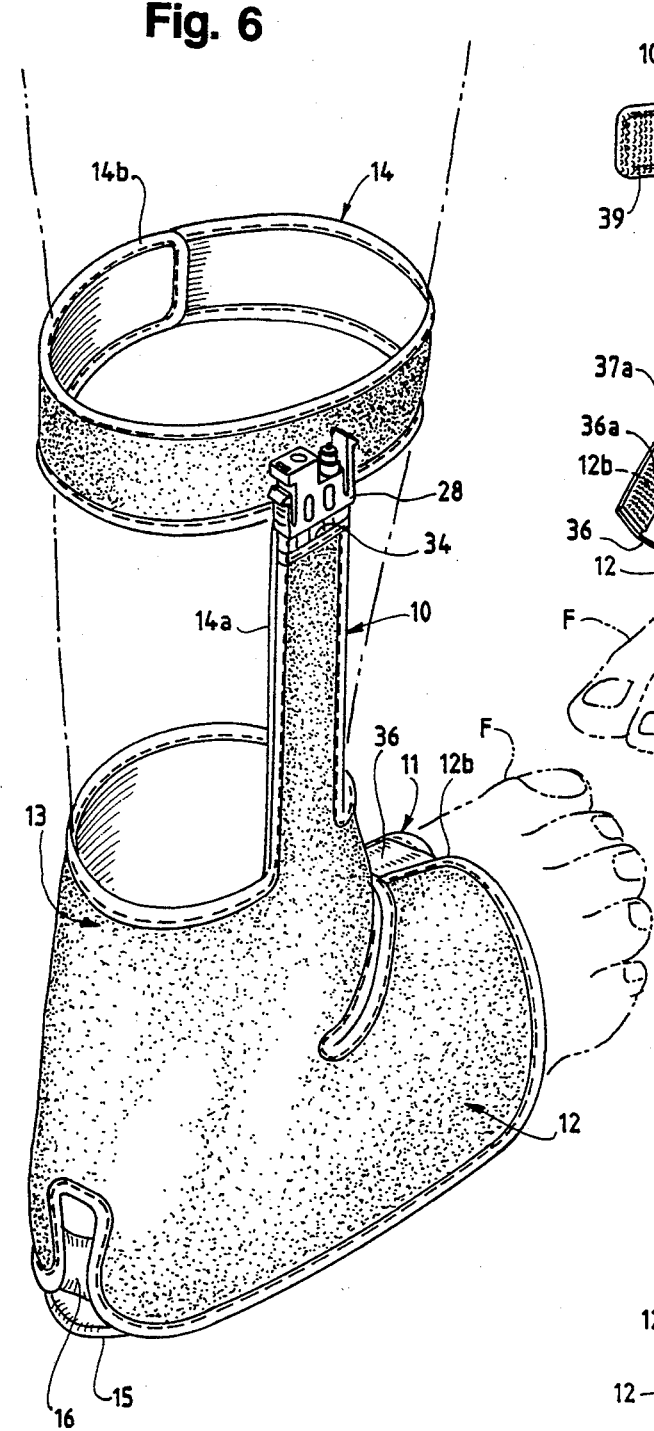
FIG. 6 is a lateral perspective view showing the blanket as properly fitted upon a wearer.
Figure 5:
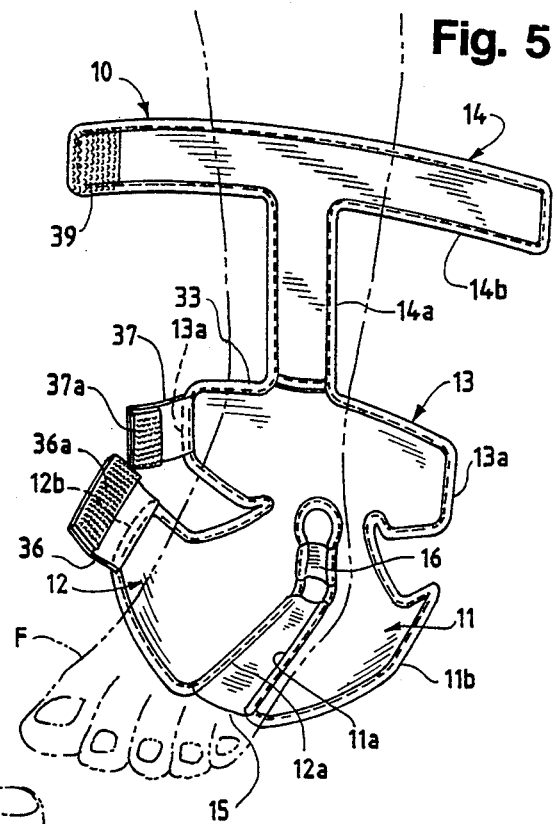
FIG. 5 is a simplified perspective view of the blanket in relation to a foot, ankle and leg about which it is to be wrapped. For clarity of illustration, the zigzag arrangement of passages, as shown in FIG. 1, is omitted from FIGS. 5–7.
Figure 7:
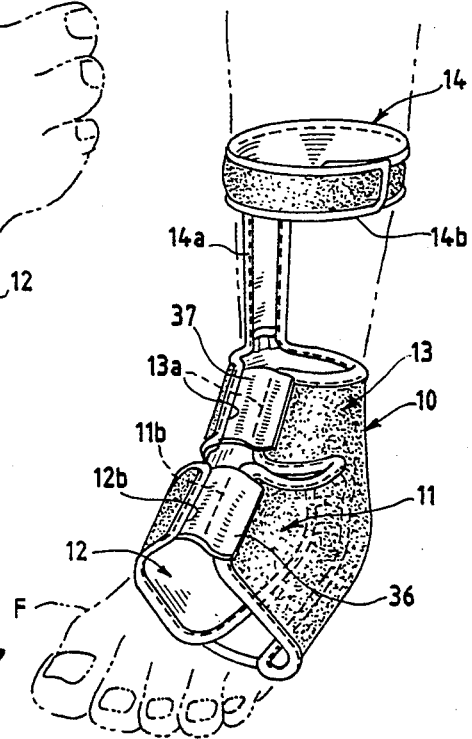
FIG. 7 is a front perspective view showing the blanket in fitted condition.

Referring to the drawings, the numeral 10 generally designates a fluid-circulating thermal blanket for post-operative treatment of the foot and ankle. The blanket is composed of multiple sections that are most clearly evident in FIG. 5. Those sections include two foot sections 11 and 12 designed for extending alongside and over the top of a wearer's foot, an ankle section 13, and a T-shaped leg wrap section 14. The sections are all integrally formed from easily-foldable sheet material, and the blanket is designed to be worn on either foot. When worn on the left foot as depicted in FIGS. 5 and 7, foot section 11 is laterally disposed and foot section 12 is medially disposed; when the blanket is worn on the right foot, the lateral/medial orientation of the two foot sections is reversed (FIG. 6).

Foot sections 11 and 12 have straight lower edges 11a and 12a joined by one or more elastic webs. In the illustration given, two such webs 15 and 16 are provided with the larger web 15 extending along the underside (sole and heel) of the wearer's foot F and the smaller web 16 extending behind the heel. The fabric of both webs is highly elastic and is stretched during application of the blanket to impose a continuous tensioning force for holding the blanket's inner surface in snug heat-transferring relation with respect to the foot and ankle. It is particularly important that the webs be stretchable in lateral directions and, ideally, the webs are formed of a material having two-way stretch capability. Elasticized fabrics having such properties are well known and widely available. Effective results have been obtained using two-way stretch fabrics formed of Antron nylon and Lycra and available under the designation "Second Skin Cloth" from Minnetonka Mills, Inc., Hopkins, Minn., but other elasticized fabrics having two-way stretch and complete return capabilities may be used.

Until web 15 is joined by stitching to the lower edges 11a, 12a of both of the foot sections 11 and 12, the blanket is capable of lying flat. Because it is formed from planar sheet materials, the blanket is therefore easy and relatively inexpensive to manufacture. The lie-flat condition is depicted in FIGS. 1 and 2 where it will be observed that one of the side edges 15a of web 15 remains unconnected to edge 11a of foot section 11. Those two edges are stitched together in a final manufacturing step to produce the contoured configuration illustrated in FIG. 5.

Sections 11-13 of the blanket are formed of inner and outer panels 18 and 19, respectively (FIG. 3). The outer panel 19 also serves as the outer panel for integral leg wrap section 14. The outer panel has its entire outer surface formed of soft loop pile fabric so that the entire outer surface of the blanket is capable of being releasably interlocked with nylon hook-providing patches of the Velcro type. The fabric of the outer panel may be multiple-layered with the outermost layer being composed of the loop-providing fabric and the other layers being a soft thermally-insulating material such as a closed-cell polyester foam backed by a nylon jersey material. Particularly effective results have been obtained using a nylon loop fabric with a polyester foam core and a nylon jersey backing marketed under the "Tempo" trademark by Lockfast, Cincinnati, Ohio, but other materials having similar properties are commercially available and may be used.

Inner panel 18 is composed of double layers 18a and 18b of thin, flexible thermoplastic sheet material heat sealed together along seal zones 20 to define at least one and preferably two serpentine fluid flow passages 22 and 23 leading from a single inlet 24 to a single outlet 25. Flexible inlet and outlet tubes 26 and 27 are sealed to and communicate with inlet 24 and outlet 25 and, at their opposite ends, the tubes are joined to a quick-disconnect fluid coupling element 28 for operatively connecting the blanket to the equipment that circulates and controls the temperature of the thermal fluid (not shown). Most advantageously, the coupling element 28 is of the hermaphroditic type as disclosed in detail in co-owned U.S. Pat. Nos. 4,982,736 and 4,951,665, the disclosures of which are incorporated by reference herein. Flow restricting means in the form of a tubular insert 29 is located in outlet tube 27 (or in the adjacent fitting of coupling element 28) for back-pressuring the system and maintaining the passages of the blanket in fluid-filled condition during operation.

Referring to FIG. 1, it will be observed that the dual passages 22 and 23 extend generally in the same directions through inner panel 18 but each such passage has a separate zigzag configuration that promotes thermal transfer and, at the same time, reduces the possibility that folding of the blanket in normal use might result in kinking and flow obstruction. In the area of each foot section, however, the directions of the dual passages are varied so that if localized forces are exerted on such passages during use of the blanket, it is unlikely that such forces will have the effect of kinking or reducing the lumen size of both passages at the same time.

The inner and outer panels 18 and 19 may be secured together along their peripheral edges in any suitable manner. Lines of stitching 31 are effectively used in the embodiment depicted in the drawings, with the edges of the panels being protected, reinforced, and finished by suitable edging tape 32.

Leg wrapping section 14 is generally T-shaped, having strap portion 14a that extends upwardly from the upper edge 33 of ankle section 13 and terminates at its upper end in a horizontally-extending band portion 14b. The T-shaped section is of double thickness, its outer wall being composed, as stated, of the loop pile material of outer panel 19. The inner wall or panel of the T-shaped section may also be composed of such loop-providing material with the pile facing either outwardly towards the other wall or inwardly. Regardless of the material used for the bodyside wall of the T-shaped section, it will be observed that the strap portion 14a of that section defines a passage which confines the flexible tubes 26 and 27, such passage having a lower opening 33 adjacent inlet 24 and outlet 25 and an upper opening 34 (FIG. 2) through which the tubes 26 and 27 protrude slightly. The coupling element 28 is disposed externally of band portion 14b so that, when the blanket is fitted upon a wearer, the coupling element is readily accessible for connecting to or disconnecting from a mating element provided by the inlet and outlet tubes of the fluid-circulating and temperature-controlling equipment. The band portion 14b also prevents direct contact between coupling element 28 and a wearer's leg.

Referring to FIG. 5, each of the foot sections 11 and 12 has an upper edge 11b and 12b with such edges extending longitudinally along a patient's instep when the blanket is in place. Similarly, ankle section 13 includes a pair of front edges 13a that extend along the front of a patient's ankle when the blanket is worn.

Velcro-type attachment means are used to adjustably and releasably connect the upper edges of the foot sections and the front edges of the ankle section. Specifically, a rectangular first fabric attachment patch 36 having a strip 36a of Velcro-type fabric with nylon hooks is connected to one of the upper edges 12b of a foot section and brought into overlapping relation with regard to the pile fabric exterior of the other foot section 11 near the upper edge 11b of that section to bring the nylon hooks of the strip 36a into interlocking engagement with the loop pile fabric of outer panel 19. Similarly, a second rectangular fabric attachment patch 37 is secured to one of the front edges 13a of the ankle section and is provided with a strip 37a of Velcro-type fabric with nylon hooks that may be brought into interlocking engagement with the pile fabric near the opposite front edge portion to secure the blanket in the fitted relation depicted in FIGS. 6 and 7. Since the patches 36 and 37 will interlock with any selected portion of loop fabric on the opposite side of the wearer's foot or ankle, a snug fit of the blanket for obtaining effective thermal exchange may be easily achieved over a wide range of foot shapes and sizes.

Attachment patches 36 and 37 are ideally formed of stretchable elastic fabric with directions of stretch and recovery extending at right angles to edges 12b and 13a, respectively. Effective results have been obtained using the same two-way stretch fabric also used for webs 15 and 16, but other elasticized fabrics having stretch and complete return capabilities are commercially available and may be used.

As the foot sections 11 and 12 are being wrapped about the sides of a wearer's foot, the elastic webs 15 and 16 and elastic attachment patches 36 and 37 should be stretched at least slightly so that they are under tensioned condition when the Velcro-type strips 36a and 37a are interlocked with the loop fabric of foot section 11 and ankle section 13. The stretchability of the patches and webs accommodates limited movement of the joint and also reduces the possibility that sudden or extreme movement might result in unintentional detachment of the hook-providing patches from the loop pile surfaces of the blanket. It also insures a close fit of the blanket over the wearer's foot and ankle and promotes effective thermal exchange when the blanket is in use. A further advantage of importance is that during the period of post-operative cryotherapy, as the swelling of the joint area diminishes, the elasticity of the webs and attachment patches allows the blanket to contract and maintain a close, comfortable, and thermally-effective fit of the blanket about the foot and ankle.

The final steps in the attachment procedure involve wrapping the band portion 14b about a wearer's leg and then securing the T-shaped leg wrap in position by bringing a Velcro-type hook-providing patch 39 at one end of the band into interlocking engagement with the loop pile fabric at the opposite end of the band. Strap portion 14a of the leg wrap, and the flexible tubes 26 and 27 contained therein, are thereby held along the medial or lateral surfaces of a wearer's leg depending on whether the blanket has been applied to the left or right foot (FIGS. 7, 6). In either case, coupling 28 is supported so that it is readily accessible, and the flexible tubes within strap portion 14a are maintained in generally linear and parallel condition, protected against twisting and kinking.

While in the foregoing, I have disclosed an embodiment of the invention in considerable detail for purposes of illustration, it will be understood by those skilled in the art that many of these details may be varied without departing from the spirit and scope of the invention.

I claim:

1. A thermal blanket for post-operative treatment of a foot and ankle, said blanket having inner and outer panels of easily-foldable material and having an outline defining two foot sections and an ankle section integral therewith; said outer panel having substantially its entire outer surface formed of soft loop pile fabric and said inner panel being composed of double layers of thermoplastic sheet material heat-sealed together to define at least one serpentine fluid-flow passage extending along a zigzag pathway from a fluid inlet opening to an adjacent fluid outlet opening; said foot sections having mutually-spaced apart bottom edges joined by a flexible elastically stretchable web positioned to underlie a patient's foot when said blanket is worn; said foot sections having upper edges adapted to extend along a patient's instep, and said ankle section having a pair of front edges adapted to extend along a front of a patient's ankle, when said blanket is worn; first attachment means for adjustably and releasably connecting together said upper edges of said foot sections; and second attachment means for adjustably and releasably connecting together said front edges of said ankle section.

2. The blanket of claim 1 in which said elastically stretchable web is capable of two-way stretch and recovery.

3. The blanket of claim 1 in which said first attachment means comprises a first attachment patch secured to said upper edge of one of said foot sections; said first attachment patch including a strip of hook-providing fabric with said hooks of said strip being releasably engagable with any selected portion of the entire outer surface of said other of said foot sections.

4. The blanket of claim 4 in which said first attachment patch is elastic and is stretchable and recoverable in directions away from and towards said upper edge of said one of said foot sections.

5. The blanket of claim 1 in which said second attachment means for adjustably and releasably connecting together said front edges of said ankle section comprises a second attachment patch secured to one of said front edges; said second attachment patch including a strip of hook-providing fabric with said hooks of said strip being releasably engagable with the pile fabric of said ankle section adjacent the other front edge of said ankle section when said blanket is fitted upon a wearer.

6. The blanket of claim 5 in which said second attachment patch is elastic and is stretchable and recoverable in directions away from and towards said one of said front edges of said ankle section.

7. The blanket of claim 1 in which a second elastically stretchable web joins said bottom edges of said foot sections behind said first-mentioned elastically stretchable web and behind a patient's heel when said blanket is worn.

8. The blanket of claim 1 in which said blanket also includes an integral T-shaped leg wrap; said leg wrap having a strap portion extending upwardly from an upper edge of said ankle portion and terminating at an upper end in a leg-encircling band portion; and third attachment means for securing said band portion in leg-encircling relation.

9. The blanket of claim 8 in which flexible inlet and outlet tubes extend longitudinally through said strap portion; said tubes having their lower ends communicating with the inlet and outlet openings of said flow passage and having upper ends connected to a quick-release fluid coupling element.

10. The blanket of claim 9 in which said outer panel with its outer surface of loop pile fabric also defines the outer surface of said T-shaped leg wrap.

11. The blanket of claim 10 in which said third attachment means for securing said band portion in leg-encircling condition comprises a patch of hook-providing material secured to said band at one end thereof and positioned to engage the outer pile fabric of said band to secure the same in leg-encircling condition when said blanket is worn.

12. The blanket of claim 11 in which said fluid coupling element is located along the outer surface of said band portion.

13. The blanket of claim 1 in which said double layers of thermoplastic material are heat sealed together to define two serpentine flow passages each extending along a separate zigzag pathway from said fluid inlet opening to said fluid outlet opening.

* * * * *